US011642650B2

(12) United States Patent
Morris et al.

(10) Patent No.: US 11,642,650 B2
(45) Date of Patent: May 9, 2023

(54) METAL ORGANIC FRAMEWORKS FOR REMOVAL OF ELEMENTAL IMPURITIES IN PHARMACEUTICAL PRODUCTS

(71) Applicant: NuMat Technologies Inc., Skokie, IL (US)

(72) Inventors: William Morris, Chicago, IL (US); Timothy Chiaan Wang, Milwaukee, WI (US); Mitchell Hugh Weston, Chicago, IL (US); Vincent Rinaolo, Chicago, IL (US)

(73) Assignee: NuMat Technologies Inc., Skokie, IL (US)

( * ) Notice: Subject to any disclaimer, the term of this patent is extended or adjusted under 35 U.S.C. 154(b) by 0 days.

(21) Appl. No.: 17/319,848

(22) Filed: May 13, 2021

(65) Prior Publication Data

US 2021/0354107 A1 Nov. 18, 2021

Related U.S. Application Data

(60) Provisional application No. 63/024,980, filed on May 14, 2020.

(51) Int. Cl.
*B01J 20/22* (2006.01)
*C01B 39/00* (2006.01)
*C07F 15/02* (2006.01)
*B01J 20/34* (2006.01)
*C07F 7/00* (2006.01)

(52) U.S. Cl.
CPC ......... *B01J 20/226* (2013.01); *B01J 20/3425* (2013.01); *C01B 39/00* (2013.01); *C07F 7/00* (2013.01); *C07F 15/02* (2013.01)

(58) Field of Classification Search
CPC ... C07C 51/418; B01J 20/226; B01J 20/3425; B01J 31/1691; B01J 31/069; B01J 31/123; C01B 39/00; C07F 7/00; C07F 15/02; C07F 7/28; B01D 2253/204
See application file for complete search history.

(56) References Cited

U.S. PATENT DOCUMENTS

| | | | |
|---|---|---|---|
| 6,235,731 B1 | 5/2001 | Shibouta et al. | |
| 8,314,090 B2 | 11/2012 | Howbert et al. | |
| 10,618,037 B2 | 4/2020 | Nakai et al. | |
| 2006/0210458 A1* | 9/2006 | Mueller | B01D 15/00 422/231 |
| 2012/0149560 A1 | 6/2012 | Lee et al. | |
| 2016/0243463 A1 | 8/2016 | Diver et al. | |
| 2019/0091503 A1 | 3/2019 | Ryu et al. | |
| 2019/0099737 A1 | 4/2019 | Srinivas et al. | |
| 2019/0111410 A1* | 4/2019 | Vallejo | B01J 20/28042 |
| 2020/0179905 A1* | 6/2020 | Genna | C07F 3/06 |
| 2020/0261885 A1* | 8/2020 | Queen | B01J 20/226 |

FOREIGN PATENT DOCUMENTS

| | | | |
|---|---|---|---|
| CN | 105107467 A | * | 12/2015 |
| CN | 105107467 A | | 12/2015 |
| CN | 106902649 | | 6/2017 |
| CN | 106902649 A | * | 6/2017 |
| CN | 109499544 A | | 3/2019 |
| TW | 202001976 | | 1/2020 |
| WO | 2017184991 A1 | | 10/2017 |
| WO | 2018206188 A1 | | 11/2018 |
| WO | 2019038645 A1 | | 2/2019 |

OTHER PUBLICATIONS

M. Kenyon et al., 48 Regulatory Toxicology and Pharmacology, 75-86 (2007) (Year: 2007).*
Z. Yin et al., 378 Coordination Chemistry Reviews, 500-512 (2019) (Year: 2019).*
Z. Bao et al., 9 Energy and Environmental Science, 3612-3641 (2016) (Year: 2016).*
M. Ahamad et al., 49 Dalton Transactions, 14690-14705 (2020) (Year: 2020).*
W. Bloch et al., Nature Chemistry (2014) (Year: 2014).*
ICH guideline Q3D (R1) on elemental impurities (2019) (Year: 2019).*
Y. Peng et al., 9 Nature Communications (2018) (Year: 2018).*
N. Galaffu et al., 11 Organic Process Research & Development, 406-413 (2007) (Year: 2007).*
H. Ly et al., 140 Journal of the American Chemical Society, 6325-6335 (2018) (Year: 2018).*
V. Pascanu et al., 19 Chemistry A European Journal, 17483-17493 (2013) (Year: 2013).*
S. Luo et al., 11 ACS Applied Materials & Interfaces 32579-32598 (2019) (Year: 2019).*
C. Garrett et al., 346 Adv. Synth. Catal., 889-900 (2004) (Year: 2004).*
C. Welch et al., 9 Organic Process Research & Development, 198-205 (2005) (Year: 2005).*
Kudzin, Zbigniew H., Phosphocysteine Derivatives; Thioureidoalkanephosphonates via Acetals, Institute of Chemistry, The University, 90-130-Lodz, Narutowicza 68, Poland, Aug. 1981, pp. 643-645.

(Continued)

*Primary Examiner* — Alexander R Pagano
(74) *Attorney, Agent, or Firm* — Paschall & Associates, LLC; James C. Paschall

(57) ABSTRACT

This invention relates to a method of using MOF adsorbents to remove elemental impurities from feed streams comprising active pharmaceutical ingredients (API). The process involves contacting the feed stream comprising API and elemental impurities with the MOF at purification conditions to obtain a purified stream with provides an API which has a concentration of the elemental impurity below its permitted daily exposure. The process can be carried in a batch mode where the MOF and feed stream are admixed in a vessel for a given amount of time or continuously by flowing the feed stream through a column or adsorbent bed containing the MOF adsorbent.

17 Claims, No Drawings

(56) References Cited

OTHER PUBLICATIONS

Deria, Pravas et al., MOF Functionalization via Solvent-Assisted Ligand Incorporations; Phosphonates vs Carboxylates, Department of Chemistry, Northwestern University, Department of Chemistry, Warsaw University of Technology, Department of Chemistry, Faculty of Science, King Abdulaziz University, Inorganic Chemistry 2015, 54, 2185-2192.

European Medicines Agency, Science Medicines Health, Committee for Human Medicinal Products, Mar. 28, 2019, 1-82.

Peng, Yaguang et al., A versatile MOF-based trap for heavy metal ION capture and dispersion, Nature Communications, (2018)9:187, 1-9.

Ke, Fei, et al., Thiol-functionalization of metal-organic framework by a facile coordination-based postsynthetic strategy and enhanced removal of Hg2+ from water. Journal of Hazardous Materials, 196 (2011), 36-43.

Google translation of CN 109499544 into English.

Google translation of TW 202001976 into English.

International Search Report and Written Opinion for corresponding application PCT/US2021/032384, dated Sep. 6, 2021.

\* cited by examiner

METAL ORGANIC FRAMEWORKS FOR REMOVAL OF ELEMENTAL IMPURITIES IN PHARMACEUTICAL PRODUCTS

CROSS-REFERENCE TO RELATED APPLICATIONS

This application claims priority from provisional application 63/024,980, filed May 14, 2020, incorporated herein in its entirety.

FIELD OF THE INVENTION

This invention generally relates to functionalized metal-organic framework (MOF) materials for the removal of contaminants such as elemental impurities e.g., palladium from Active Pharmaceutical Ingredient (API) process streams. The invention also relates to a process for purifying API process streams using a MOF.

BACKGROUND OF THE INVENTION

In March 2019, the International Council for Harmonization (ICH) of Technical Requirements for Pharmaceuticals for Human Use issued its guidelines for elemental impurities in pharmaceutical products, Q3D(R1). These guidelines dictate the levels of elemental impurities which are allowed in pharmaceutical products. The elements are divided into three classes based on their Permitted Daily Exposure (PDE). Class 1 lists As, Cd, Hg, and Pb metals which are human toxicants and are present in drugs as a result of impurities in chemicals used to manufacture the drugs or active pharmaceutical ingredients (API). Class 2 is divided into class 2A and 2B. Class 2A elements are Co, V, and Ni, while class 2B elements are Ag, Au, Ir, Os, Pd, Pt, Rh, Ru, Se, and Tl. These elements are generally present in API owing to their use in synthesizing APIs. The elements in class 2A have a greater probability of being present in the API versus those in class 2B. Class 3 elements are Ba, Cr, Cu, Li, Mo, Sb, and Sn. Class 3 elements are considered to have lower toxicity than elements in classes 1 or 2.

Most of the elements in class 2 are present because they're used as catalysts in the synthesis of API and thus after the API is synthesized, the elements must be removed from the API process stream so that their concentration is below their PDE. Scavengers which have been used in the industry to remove elemental impurities use silica, polymer resins or polymer fibers as a base to which are attached functional groups which can bind to the elements. These functional groups include sulfur or nitrogen containing groups such as mercaptans, amines (both alkyl and aryl), etc. The amount of scavenger needed to remove the particular metal can be quite large or it may be necessary to pass the API solution through multiple columns in order to achieve the necessary reduction in elemental impurity concentration. Also, these scavengers are generally hard to regenerate and thus, fresh scavenger material needs to be used each time.

In order to meet this need, Applicants have developed scavengers based on metal-organic framework (MOF) materials. MOFs are well known porous adsorbents which have high surface areas. MOF adsorbents comprise metal ion corner atoms and at least a bidentate linker molecule or a ligand, which is connected to the corner atom(s) thereby forming a framework structure. Functional groups having sulfur or nitrogen in their structures can be bound to the framework in various ways thus allowing elements such as palladium to bind to MOF and be removed from the API process stream. Applicants have found that MOFs are more efficient than scavengers of the prior art and thus present a substantial improvement over the scavengers of the prior art.

SUMMARY OF THE INVENTION

One embodiment of the invention is a process for purifying a feed stream comprising an active pharmaceutical ingredient (API) and a contaminant, the process comprising contacting the feed stream with an adsorbent at purification conditions to adsorb at least a portion of at least one contaminant onto the adsorbent and provide a purified API stream; wherein the adsorbent is a metal organic framework (MOF) comprising metal ion corner atoms and a linker molecule which is at least a bidentate ligand, the MOF further having at least one functional moiety which is able to bind with at least one contaminant in the feed solution.

Another embodiment is where the contaminant is an elemental impurity selected from at least one element from class 1, class 2A, class 2B, and class 3 of the ICH Q3D(R1) guidelines.

Yet another embodiment is where the adsorbent adsorbs a quantity of the elemental impurity in the feed stream to provide a purified API stream having a concentration of the elemental impurity which calculates to a concentration of the elemental impurity in a recovered API which is at or below its Permitted Daily Exposure (PDE).

In one embodiment, the process of purification is carried out in a vessel as a batch process.

In another embodiment, the purification is carried out as a continuous process. When the purification is carried out as a continuous process, the feed stream can be flowed through a bed of adsorbent either in a single pass or in multiple passes.

Yet other embodiments are where the stream is contacted with the adsorbent at a pressure from about 0.01 kPa to about 1000 kPa or at temperatures from about −50° C. to about 120° C. or about −20° C. to about 100° C. or about 0° C. to about 80° C. or from about 10° C. to about 70° C. or from about 20° C. to about 60° C.

A still further embodiment is where the feed stream is admixed with the adsorbent and is contacted for a time from about 5 sec to about 3 days or from about 1 minute to about 1 day.

Another embodiment of the invention is where the functional moiety on the MOF that binds to at least one contaminant is at least one molecule selected from an inorganic molecule containing at least one sulfur or nitrogen or phosphorous or oxygen atom, or an organic molecule having an alkyl backbone having from 1 to 10 carbon atoms, or an aryl or heteroaryl backbone having from 1 to 5 aryl or heteroaryl groups and containing at least one of a sulfur or nitrogen or phosphorous or oxygen atom in its structure, or substituted phosphonic acids having the formula $P(OH)_2OR$ where R is a heteroalkyl group having from 1 to 15 carbon atoms and contains at least one of a sulfur or nitrogen atom in its structure.

In a particular embodiment, the functional moiety is selected from thioglycolic acid (TGA), thiourea, 4-mercapto pyridine, 2,4,6,-trimercaptotriazine (TMT), 1,4,7,10-Tetraazacyclododecane-1,4,7,10-tetraacetic acid (DOTA), ethylenediaminetetraacetic acid (EDTA), thiosulfate (TS), mercaptomethyl phosphonic acid (MPA), trimercaptotriazine-methyl-phosphonic acid (TMT-PA), and mixtures thereof.

In a further particular embodiment, the functional moiety is attached to a metal site or is covalently bonded to the framework.

Yet a further embodiment is where the metal ion of the MOF is selected from $Li^+$, $Na^+$, $K^+$, $Rb^+$, $Be^{2+}$, $Mg^{2+}$, $Ca^{2+}$, $Sr^{2+}$, $Ba^{2+}$, $Sc^{3+}$, $Y^{3+}$, $Ti^{4+}$, $Zr^{4+}$, $Hf^4$, $V^5$, $V^{4+}$, $V^{3+}$, $Nb^{3+}$, $Ta^{3+}$, $Cr^{3+}$, $Cr^{2+}$, $Mo^{3+}$, $W^{3+}$, $Mn^{3+}$, $Fe^{3+}$, $Fe^{2+}$, $Ru^{3+}$, $Ru^{2+}$, $Os^{3+}$, $Os^{2+}$, $Co^{3+}$, $Co^{2+}$, $Ni^{2+}$, $Ni^+$, $Pd^{2+}$, $Pd^+$, $Pt^{2+}$, $Pt^+$, $Cu^{2+}$, $Cu^+$, $Ag^+$, $Au^+$, $Zn^{2+}$, $Al^{13+}$, $Ga^{3+}$, $In^{3+}$, $Si^{4+}$, $Si^{2+}$, $Ge^{4+}$, $Ge^{2+}$, $Sn^{4+}$, $Sn^{2+}$, $Bi^{5+}$, $Bi^{3+}$, $Cd^{2+}$, $Mn^{2+}$, $Tb^{3+}$, $Gd^{3+}$, $Ce^{3+}$, $La^{3+}$ and $Cr^{4+}$, and mixtures thereof.

In a particular embodiment, the metal ion is selected from $Ti^{4+}$, $Zr^{4+}$, $Hf^{4+}$, $Fe^{3+}$, $Fe^{2+}$, $Co^3$, $Co^{2+}$, $Ni^{2+}$, $Ni^+$, $Cu^{2+}$, $Cu^+$, $Zn^{2+}$, $Al^3$ and mixtures thereof.

In a more particular embodiment, the metal ion is selected from $Ti^{4+}$, $Zr^{4+}$, $Fe^{3+}$, $Co^{3,S}$, $Ni^{2+}$, $Cu^{2+}$, $Zn^{2+}$, $Al^3$ and mixtures thereof.

A further embodiment of the process is where the linker molecule is selected from one or more ligands comprising a saturated or unsaturated alkyl or aryl backbone, optionally comprising one or more heteroatoms S, N, O, or P, and optionally comprising one or more functional groups bound to the backbone, each ligand comprising two or more sites capable of binding to a metal ion corner atom, thereby forming a metal organic framework. In some embodiments inorganic linkers also can be present.

A particular embodiment is where the linker is selected from substituted or unsubstituted mono- or polynuclear aromatic di-, tri-, and tetra-carboxylic acids, and substituted or unsubstituted at least one hetero atom comprising aromatic di-, tri-, and tetra-carboxylic acids which have one or more nuclei and mixtures thereof.

A more specific embodiment is where the linker is selected from 1,3,5-benzene tricarboxylic acid (BTC), 4,4',4"-s-Triazine-2,4,6-triyl-tribenzoic acid ($H_3TATB$), 2-amino-terephthalic acid, naphthalene dicarboxylate (NDC), acetylene dicarboxylate (ADC), benzene-1,4-dicarboxylic acid (BDC), benzene tribenzoate (BTB), methane tetrabenzoate (MTB), adamantane tetracarboxylate (ATC), adamantane tribenzoate (ATB), 4,4',4",4'"-(pyrene-1,3,6,8-tetrayl)tetrabenzoic acid (TBAPy), meso-Tetraphenylporphine-4,4',4",4'"-tetracarboxylic acid (TCPPH2), 1,4-diazabicyclo[2.2.2]octane (DABCO) and mixtures thereof.

In yet a further embodiment, the MOF with the functional moiety is selected from MOF-808-TGA, MOF-808-TS, MOF-808-TU, MOF-808-SHPy, MOF-808-MPA, PCN-777-TGA, PCN-777-TS, PCN-777-TU, MIL-101-SHPy, MIL-101-TGA, MIL-101-TS, MIL-101-TU, and mixtures thereof.

These and other aspects and embodiments of the invention will become clearer after a detailed description of the invention.

DETAILED DESCRIPTION OF THE INVENTION

As stated, this invention generally relates to a process for removing contaminants such as elemental impurities from solution or streams comprising active pharmaceutical ingredients (API). Generally, the process involves contacting the API containing stream with an adsorbent which is a metal-organic framework which will be described in detail below. The conditions under which the feed stream is contacted with the MOF adsorbent will also be described in detail.

In June 2013, the International Council for Harmonization (ICH) of Technical Requirements for Pharmaceuticals for Human Use established guidelines for the amount of elemental impurities in drug products. The latest guidelines labeled Q3D (R1) were adopted in March 2019. Elemental impurities are present in drug products either because of impurities or residual amounts of catalytic metals. Since these elemental impurities do not provide any therapeutic benefit to the patient, they must be controlled within a narrow range. The ICH, based on toxicity data of elemental impurities, established a Permitted Daily Exposure (PDE) for each elemental impurity. A PDE for each elemental impurity was calculated based on the route of administration, i.e. oral, parenteral or inhalation and the amount of drug taken per day. The ICH further grouped the elemental impurities into several classes. Class 1 is composed of elements As, Cd, Hg, and Pb which are human toxicants and have little or no use in the manufacture of pharmaceuticals. Class 2 is further broken down into Class 2A and Class 2B. The elements in class 2 are route-dependent (how administered) human toxicants. The elements in Class 2A have a higher probability of occurring in pharmaceuticals. Class 2A elements are Co, Ni and V. Class 2B elements which have a lower probability of being present are Ag, Au, Ir, Os, Pd, Pt, Rh, Ru, Se, and Tl. C lass 3 elements have a lower toxicity for oral administration and are Ba, Cr, Cu, Li, Mo, Sb, and Sn. The PDE for the various elemental impurities and the route of administration are presented in Table A.2.1 from the guidelines and is reproduced below.

TABLE A.2.1

Permitted Daily Exposure for Elemental Impurities[1]

| Element | Class | Oral PDE µg/day | Parenteral PDE, µg/day | Inhalation PDE, µg/day |
| --- | --- | --- | --- | --- |
| Cd | 1 | 5 | 2 | 3 |
| Pb | 1 | 5 | 5 | 5 |
| As | 1 | 15 | 15 | 2 |
| Hg | 1 | 30 | 3 | 1 |
| Co | 2A | 50 | 5 | 3 |
| V | 2A | 100 | 10 | 1 |
| Ni | 2A | 200 | 20 | 5 |
| Ti | 2B | 8 | 8 | 8 |
| Au | 2B | 100 | 100 | 1 |
| Pd | 2B | 100 | 10 | 1 |
| Ir | 2B | 100 | 10 | 1 |
| Os | 2B | 100 | 10 | 1 |
| Rh | 2B | 100 | 10 | 1 |
| Ru | 2B | 100 | 10 | 1 |
| Se | 2B | 150 | 80 | 130 |
| Ag | 2B | 150 | 10 | 7 |
| Pt | 2B | 100 | 10 | 1 |
| Li | 3 | 550 | 250 | 25 |
| Sb | 3 | 1200 | 90 | 20 |
| Ba | 3 | 1400 | 700 | 300 |
| Mo | 3 | 3000 | 1500 | 10 |
| Cu | 3 | 3000 | 300 | 30 |
| Sn | 3 | 6000 | 600 | 60 |
| Cr | 3 | 11000 | 1100 | 3 |

[1]Table A.2.1 is reproduced with permission from the ICH Guideline Q3D (R1) which may be accessed at https://www.ema.europa.eu/en/documents/scientific-guideline/international-conference-harmonisation-technical-requirements-registration-pharmaceuticals-human-use_en-32.pdf.

One aspect of the invention is a feed stream or feed solution (terms will be used interchangeably) which contains an API and one or more contaminants, e.g. the elemental impurities enumerated above. The stream or solution comprises either an organic solvent or an aqueous solvent. The solvent may be the solvent which was used to synthesize the API, or if more than one step is needed to synthesize the API the solvent may be the solvent used in the last reaction step or the solvent used to purify the API. Exemplary solvents include but are not limited to water, methanol, ethanol, isopropanol, butanol, t-butyl alcohol, acetone, dimethyl sulfoxide, dimethylformamide, ethyl acetate, isopropyl acetate, methyl-tertbutyl ether, diethyl ether, dichloromethane, chloroform, benzene, toluene, xylene, hexanes, dichlorobenzene, acetonitrile, N-methyl-2-pyrrolidone, 4-dimethylamino-pyridine, hexamethylphosphoramide, tetrahydrofuran, ethylene glycol, and mixtures thereof.

The feed stream can also contain contaminants which include but are not limited to additives, by-products, unreacted starting materials, and catalyst degradation products. Although the process described below can be used to remove elemental impurities, and/or other contaminants, the process will be described using elemental impurities, but it is to be understood that the process is not limited to removing only elemental impurities.

Another aspect of the invention is the use of an adsorbent which is a metal-organic framework (MOF) to remove contaminants from an active pharmaceutical ingredient process stream. MOFs are well known porous adsorbents which have high surface areas. MOF adsorbents comprise metal ion corner atoms and at least a bidentate linker molecule or a ligand, which is connected to the corner atom(s) thereby forming a framework structure. The metal ions which can be used include but are limited to $Li^+$, $Na^+$, $K^+$, $Rb^+$, $Be^{2+}$, $Mg^{2+}$, $Ca^{2+}$, $Sr^{2+}$, $Ba^{2+}$, $Sc^{3+}$, $Y^{3+}$, $Ti^{4+}$, $Zr^{4+}$, $Hf^{4+}$, $V^{5+}$, $V^{4+}$, $V^{3+}$, $Nb^{3+}$, $Ta^{3+}$, $Cr^{3+}$, $Cr^{2+}$, $Mo^{3+}$, $W^{3+}$, $Mn^{3+}$, $Fe^{3+}$, $Fe^{2+}$, $Ru^{3+}$, $Ru^{2+}$, $Os^{3+}$, $Os^{2+}$, $Co^{3+}$, $Co^{2+}$, $Ni^{2+}$, $Ni^+$, $Pd^{2+}$, $Pd^+$, $Pt^{2+}$, $Pt^+$, $Cu^{2+}$, $Cu^+$, $Ag^+$, $Au^+$, $Zn^{2+}$, $Al^{3+}$, $Ga^{3+}$, $In^{3+}$, $Si^{4+}$, $Si^{2+}$, $Ge^{4+}$, $Ge^{2+}$, $Sn^{4+}$, $Sn^{2+}$, $Bi^{5+}$, $Bi^{3+}$, $Cd^{2+}$, $Mn^{2+}$, $Tb^{3+}$, $Gd^{3+}$, $Ce^{3+}$, $La^{3+}$ and $Cr^{4+}$, and mixtures thereof. Particular metal ions are selected from $Ti^{4+}$, $Zr^{4+}$, $Hf^{4+}$, $Fe^{3+}$, $Fe^{2+}$, $Co^{3+}$, $Co^{2+}$, $Ni^{2+}$, $Ni^+$, $Cu^{2+}$, $Cu^+$, $Zn^{2+}$, $Al^{3+}$ and mixtures thereof. A more particular group of metal ions are selected from $Ti^{4+}$, $Zr^{4+}$, $Fe^{3+}$, $Co^{3+}$, $Ni^{2+}$, $Cu^{2+}$, $Zn^{2+}$, $Al^{3+}$ and mixtures thereof.

The metal ion corner atoms are joined by at least bidentate organic linker molecules comprising two or more sites capable of binding to a metal ion corner atom to form a metal organic framework structure. Optionally, at least bidentate inorganic linker molecules also can be used. The at least bidentate organic linker molecules include but are not limited to those having a saturated or unsaturated alkyl or aryl backbone, optionally comprising one or more heteroatoms S, N, O, or P, and optionally comprising one or more functional groups bonded to the backbone. In certain embodiments the linker backbone can comprise one or more groups selected from 1) saturated or unsaturated, linear, branched or cyclic alkyl groups having from 1 to 10 carbon atoms and optionally comprising heteroatoms; and 2) groups comprising 1 to 5 aryl or heteroaryl rings which can be fused or joined covalently; wherein the hetero atoms are selected from S, N, O, P and mixtures thereof. The backbones of the linker molecules may have bonded thereto one or more functional groups, including but not limited to saturated and unsaturated alkyl, aryl, heteroaryl, halide, —OH, —$NH_2$, —COOH, $NO_2$, COH, CO($NH_2$), CN and thiols. In one embodiment the functional groups are selected from —COOH and $NH_2$.

Particular ligands which can used include without limitation 1,3,5-benzene tricarboxylic acid, ADC (acetylenedicarboxylate), NDC (naphtalene dicarboxylate), BDC (benzene-1,4-dicarboxylic acid), ATC (adamantane tetracarboxylate), BTB (benzene tribenzoate), MTB (methane tetrabenzoate), 2-amino terephthalic acid, 4,4',4'',4'''-(pyrene-1,3,6,8-tetrayl)tetrabenzoic acid (TBAPy), meso-tetraphenylporphine-4,4',4'',4'''-tetracarboxylic acid (TCPPH2), ATB (adamantane tribenzoate), DABCO (1,4-diazabicyclo[2.2.2]octane), 4,4',4''-s-Triazine-2,4,6-triyl-tribenzoic acid ($H_3TATB$) and mixtures thereof.

Specific MOFs which can be used in the invention include but are not limited to MOF-808 ($Zr_6O_4(OH)_4(BTC)_2(OH)_6$ ($H_2O)_6$), PCN-777 ($Zr_6O_4(OH)_4(TATB)_2(OH)_6(H_2O)_6$), MIL-101($Fe_3O(BDC)_3(OH)$ $(H_2O)_2$), MIL-101-$NH_2$ ($Fe_3O$ ($NH_2$-BDC)$_3$(OH) ($H_2O)_2$), and mixtures thereof.

The MOFs of the invention also have a functional moiety which can bind to the elemental impurity, such as those functional moieties having a high metal affinity. The functional moieties which are active for binding with an elemental impurity include but are not limited to those molecules which contain at least one of a sulfur or nitrogen atom in their structure, or substituted phosphonic acids having the formula $P(OH)_2OR$ where R is an alkyl group having from 1 to 15 carbon atoms and contains at least one of a sulfur or nitrogen atom in its structure. In certain embodiments the functional moieties can include an alkyl backbone having from 1 to 10 carbon atoms or an aryl backbone having from 1 to 5 aryl or heteroaryl rings. Specific examples of suitable functional moieties include but are not limited to thioglycolic acid (TGA), thiourea, 4-mercapto pyridine, 2,4,6,-trimercaptotriazine (TMT), 1,4,7,10-Tetraazacyclododecane-1,4,7,10-tetraacetic acid (DOTA), ethylenediaminetetraacetic acid (EDTA), thiosulfate (TS), mercapto phosphonic acid (MPA), and mixtures thereof.

The functional moiety can be introduced into the MOFs by grafting molecules containing the functional moiety onto an open coordination site of the metal ion corner atoms, by replacing the existing linkers with these molecules, or by covalently bonding the molecules to the framework. The functional moiety is introduced to the framework by reacting the MOF with the molecule containing the desired functional moiety in a suitable solvent at treatment conditions. Suitable solvents include but are not limited to tetrahydrofuran, methanol, chloroform, dimethylformamide and dimethylsulfoxide. Treatment conditions include a temperature from about 10° C. to about 100° C. for a time of about 1 hour to about 2 days. The treated MOF is then isolated by know methods such as filtration or centrifugation and dried at a temperature from about 25° C. to about 150° C. for a time of about 1 hour to about 2 days to provide the functional moiety containing MOF.

As will be detailed below specific MOFs with specific moieties which can be used in the practice of the invention include but are not limited to MOF-808-TGA, MOF-808-TS, MOF-808-TU, MOF-808-SHPy, MOF-808-MPA, PCN-777-TGA, PCN-777-TS, PCN-777-TU, MIL-101-SHPy, MIL-101-TGA, MIL-101-TS, MIL-101-TU, and mixtures thereof.

There are several ways to prepare MOF compositions but the most commonly used one is the solvothermal synthesis. For example, see Yujia Sun and Hong-Cai Zhou, Recent Progress in the Synthesis of Metal Organic Frameworks, *Sci. Technol. Adv. Mater.* 16 (2015), 054202. In this procedure a metal salt and the desired ligand/linker are dissolved in an appropriate solvent and reacted at room temperature or an elevated temperature for a required time. Once the MOF is formed, the powder is isolated from the reaction mixture, washed and dried.

Although the MOF compositions of the invention can be used in the powder form, it may be advantageous to form the MOF composition into various shaped bodies such as pellets, spheres, disks, monolithic bodies, irregularly shaped particles and extrudates. The methods of forming these types of shapes are well known in the art. The MOF materials can be formed into various shapes by themselves or by including a binder. When selecting a binder, it is important to select a binder such that the surface area and adsorption capacity is not adversely affected once the desired shaped body is formed. Materials which can be used as binders include without limitation cellulose, silica, carbon, alumina, and mixtures thereof.

The forming process usually involves preparing a thick paste-like material by mixing the MOF composition with a solvent or a binder plus a solvent. Once the paste-like material is formed it can be extruded through a die having holes of about 1-2 mm to form extrudates of varying length, e.g., 6-10 mm. The paste or even the powder itself can be pressed at high pressure to form pellets or pills. Other means of forming shapes include pressure molding, metal forming, pelletizing, granulation, etc.

In yet another aspect of the invention, the MOF adsorbent can be deposited onto articles such as, but not limited to, monoliths, spherical supports, ceramic foams, glass fibers, woven fabrics, nonwoven fabrics, membranes, pellets, extrudates, irregularly shaped particles, and mixtures thereof. When the desired article is a monolith, spherical support, ceramic foam, pellets, extrudates, or irregularly shaped particles, a slurry of the MOF composition is prepared and deposited on the article by means such as dipping, spray drying, etc. followed by drying and optionally calcination. The MOF composition can also be directly synthesized on the membrane. The MOF compositions of the invention can be deposited or dispersed onto fabrics (woven and non-woven) or polymers by techniques such as electrospinning, direct crystal growth, and layer by layer deposition.

The MOF materials whether in powder form or in a shaped form are now contacted with the feed stream at purification conditions in order for the MOF adsorbent to adsorb and remove the unwanted elemental impurity from the feed stream and provide a purified API stream. The MOF and API comprising feed stream may be contacted in a batch system by admixing the feed stream and MOF in a suitable vessel to provide the purified API stream. The mixture is now at purification conditions which includes a temperature of about −50° C. to about 120° C. or about −20° C. to about 100° C. or about 0° C. to about 80° C. or from about 10° C. to about 70° C. or from about 20° C. to about 60° C. Another purification condition is the time required to achieve the desired removal of elemental impurity. This contact time can vary considerably and is dependent on the contact temperature, pH of the feed stream and pressure. Generally, the contact time is from about a few seconds to several days, more specifically from about 5 seconds to about 3 days, or from about 1 minute to about 1 day, or from about 10 minutes to about 18 hours or from about 20 minutes to about 12 hours, or from about 40 minutes to about 8 hours or from about 1 hour to about 6 hours. Optionally the mixture can be stirred or agitated to increase contact between the MOF and feed stream in order to decrease the time required to achieve the desired final concentration of the metal impurity. Agitation can be carried out by using a shaking table or other suitable device. Stirring can be carried out using a mechanical stirrer and the stirring rate is adjusted to provide from about 0.2 turnovers per minute to about 15 turnovers per minute or from about 0.5 turnovers per minute to about 10 turnovers per minute or from about 1 turnover per minute to about 8 turnovers per minute. If it is determined that after a given amount of time the concentration has reached a plateau, but the elemental impurity concentration is still above the required limit, the API stream can be separated from the MOF and the API stream contacted with a fresh quantity of MOF. The w/w % i.e., weight of MOF/weight of stream, between the two purification steps does not have to be the same. That is, the amount of MOF used in the first step can be more or less than the MOF in the second step. For example, w/w % in the first step can vary from about 0.1 w/w % to about 70 w/w % or from about 0.5 w/w % to about 60 w/w % or from about 1 w/w % to about 50 w/w % or from about 2 w/w % to about 40 w/w % or from about 5 w/w % to about 30 w/w % or from about 1 w/w % to about 30 w/w % or from about 0.5 w/w % to about 60 w/w % or from about 1 w/w % to about 50 w/w % or from about 2 w/w % to about 40 w/w % or from about 5 w/w % to about 30 w/w %. In the second step the w/w % can vary from about 0.1 w/w % to about 70 w/w % or from about 0.5 w/w % to about 60 w/w % or from about 1 w/w % to about 50 w/w % or from about 2 w/w % to about 40 w/w % or from about 5 w/w % to about 30 w/w %.

Another parameter which can be adjusted is the pH of the feed stream. The pH can have an effect on the affinity of the functional moiety for the specific elemental impurity being removed. The optimum pH or pH range can be different for different functional moieties and this optimum pH or range can be determined experimentally.

The adsorbent used in the above-described batch process can be a mixture of two or more MOFs in order to optimize the removal of multiple elemental impurities. It can be experimentally determined which MOFs better adsorb one elemental impurity versus another and thus an optimum mixture of MOFs can be obtained to purify any API feed stream based on the makeup of the elemental impurities in the feed stream. The two or more MOFs can be mixed together and formed into shaped articles such as spheres, extrudates, etc. as described above. Alternatively, instead of using a mixture of MOFs in one vessel, the process can be carried out by admixing the API feed stream with a first MOF in one vessel, separating (by well-known means) the MOF from the partially purified stream and then admixing the partially purified stream with a second MOF is a second vessel at similar or different purification conditions to provide the purified API stream.

It is also within the scope of the invention that the amount of the two MOFs can be different. The relative amount of each MOF can vary substantially based on the affinity of a MOF for a particular elemental impurity or the total capacity of the MOF for the elemental impurity. The purification conditions used for each MOF (if used in different vessels) can also be adjusted to optimize elemental impurity removal. The maximum concentration of the elemental impurity in the purified API stream which must be achieved is dependent on the PDE of the elemental impurity, the concentration of the elemental impurity in the API feed stream and the final concentration of the elemental impurity in the API (Table A.2.1).

In another aspect of the invention, the method is carried out as a continuous process in which the MOF is placed in a bed through which flows the feed stream comprising the API and the one or more contaminants. In one embodiment the bed can be in the form of a rigid configuration such as a column. The column can have any type of shape such as square, rectangular or circular. Circular columns are the most common type of columns. The feed stream is introduced through one or more inlet ports and the feed stream flowed downward or upward through the column. In a particular aspect of the invention two or more inlet ports are used in order to ensure uniform distribution of the feed stream radially across the column. The one or more inlet ports can be spaced around the circumference of the column. When the feed stream is down flowed a particular arrangement is a shower arrangement or configuration which is located at the top end or cap of the column allowing a shower of feed stream to contact the MOF with the most even distribution radially across the column.

The inlet ports can have any shape well known in the art such as orifices whose outlet diameter and shape determines the area and flow pattern that the orifice can cover. The purified API stream is removed from an outlet port and passed to other vessels or reactors to isolate the API.

The column is sized depending on the amount of feed stream to be purified. The ratio of the height to the diameter of a column can vary considerably. Factors to be taken into considerations include the amount of back pressure created, flow rate of the feed stream, i.e., contact time, the amount of drug to be purified, the purification levels necessary, and the efficacy of the column media. For example, a high ratio of height: diameter may create more backpressure and increase the time required to pass the feed stream through the column. A low (or lower) height: diameter ratio will decrease the backpressure, but the contact time will be shorter and radial flow distribution may not be as even. Using computational fluid dynamics (CFD) one can model various configurations and arrive at an optimum configuration.

In order to ensure that elemental impurity concentration of the purified stream meets the ICH guidelines for the particular elemental impurity, the flow rate needs to be controlled to ensure sufficient contact time between the feed stream and the MOF since the contact time is dependent on the flow rate of the feed stream and the size of the reactor, i.e. the cross-sectional area of the reactor. Linear velocity is a parameter which takes into account the size of the reactor and thus is a better parameter to use. The linear velocity can range from about 0.02 to about 300 cm/min. or from about 0.05 to about 200 cm/min. or from about 0.1 to about 100 cm/min. or from about 0.2 to about 50 cm/min.

The column can be operated over a broad temperature range. The low end of the range is dependent on the temperature the API starts to precipitate from the solution. The temperature varies from about −50° C. to about 120° C. or about −20° C. to about 100° C. or about 0° C. to about 80° C. or from about 10° C. to about 70° C. or from about 20° C. to about 60° C. Although the column can be operated at atmospheric pressure, it can be operated over a wide pressure range from below atmospheric pressure to above atmospheric pressure. Generally, the pressure range can be from about 0.01 kPa to about 1000 kPa or from about 5 kPa to about 500 kPa or from about 10 kPa to about 200 kPa or from about 20 kPa to about 100 kPa.

Although only one MOF material can be used in the column, as stated above if the feed stream contains more than one elemental impurity, it may be advantageous to use more than one MOF. In this case the different MOFs can be first mixed together and used to fill the column. Alternatively, the two or more MOFs can be placed in the column in alternating layers. The layers do not need to be of equal size but can be sized depending on the affinity of the MOF for a particular elemental impurity or the adsorption capacity of the MOF(s) for an elemental impurity or the concentration of the elemental impurity in the feed stream. The order of the MOFs in the column is also determined by the affinity and adsorption capacity of each MOF for the various elemental impurities. It is also possible to use a plurality of columns, and in which the adsorbents in each column can be the same or different.

If the stream exiting the purification column has a concentration of the one or more elemental impurities above its PDE, then the exit stream may either be passed through the same column a second time or multiple times. This can be accomplished by the use of a circulation loop on the side of the column or reactor which takes an exit stream from a loop outlet port proximate to the outlet port and passes the stream to a loop inlet port on the column or reactor proximate to the inlet port. Alternatively, the exit stream may be passed through a second column containing fresh MOFs. The second column can contain the same MOFs as the first column or different MOFs or a different axial arrangement of the MOFs. A particular aspect of the invention is where the feed stream is flowed through the purification column once and the exit stream is the purified stream which meets the ICH guidelines for elemental impurities.

Once the MOF has reached its adsorption capacity whether it is used in a batch or continuous column process it can be either disposed or regenerated. In a particular aspect of the invention the MOF is regenerated so that it can be reused in the process. In the case where the process is a continuous process using a column configuration, the MOF can be regenerated by flowing a solvent through the column at regeneration conditions. The solvents which can be used to regenerate the MOF include but are not limited to water, methanol, ethanol, isopropanol, butanol, t-butyl alcohol, acetone, dimethyl sulfoxide, dimethylformamide, ethyl acetate, isopropyl acetate, methyl-tertbutyl ether, diethyl ether, dichloromethane, chloroform, benzene, toluene, xylene, hexanes, dichlorobenzene, acetonitrile, N-methyl-2-pyrrolidone, 4-dimethylamino-pyridine, hexamethylphosphoramide, tetrahydrofuran, ethylene glycol, and mixtures thereof.

The solvent is flowed through the column at a linear velocity from about 0.02 to about 300 cm/min. or from about 0.05 to about 200 cm/min. or from about 0.1 to about 100 cm/min. or from about 0.2 to about 50 cm/min. The temperature at which the contacting is carried out can vary from about −50° C. to about 120° C. or about −20° C. to about 100° C. or about 0° C. to about 80° C. or from about 10° C. to about 70° C. or from about 20° C. to about 60° C. Regeneration can be carried out at atmospheric pressure or pressure from below atmospheric to above atmospheric pressure. Generally, the pressure can be from about 0.01 kPa to about 1000 kPa or from about 5 kPa to about 500 kPa or from about 10 kPa to about 200 kPa or from about 20 kPa to about 100 kPa. The advantage to regenerating the MOF in the purification column is that by employing multiple columns, one column can be regenerated while another is actively purifying a feed stream. This is usually referred to as a swing reactor operation.

In addition to regenerating the MOF in situ, the MOF can be removed from the column or in the case of batch operation it is removed from the reaction or purification vessel and regenerated in a separate vessel. The conditions set forth above, i.e., temperature and pressure are the same as set forth above for the in-situ operation. However, instead of flow rate, contact time is varied. Contact time can vary from about 1 minute to about 72 hours or from about 5 minutes to about 48 hours or from about 20 minutes to about 24 hours or from about 40 minutes to about 12 hours or from about 1 hour to about 8 hours. Additionally, the resulting mixture can be stirred to increase contact between the solvent and MOF. Once the MOF is regenerated, it is separated from the solvent by well-known means such as filtration, centrifugation, etc. dried and is ready to be used again in a purification process.

EXAMPLES

Example 1: MOF-808 Synthesis

MOF-808 was synthesized using the procedure reported in *J. Am. Chem. Soc.* 2014, vol. 136(37), 12844-12847. In a 1-L Pyrex jar zirconyl chloride hydrate (9.7 g) and 1,3,5 benzene tricarboxylic acid (2.1 g) were dissolved in DMF/formic acid (450 mL/450 mL) to form a mixture. The reaction mixture was heated at 130° C. in an oven for 24 h, and the resulting white solid precipitate was separated by filtration. The MOF was then washed with DMF and soxhlet extracted with acetone to remove unreacted precursor and was dried at 150° C. under vacuum.

Example 2: Synthesis of PCN-777 MOF

PCN-777 was synthesized using a modified procedure based on the synthesis reported in *Angewandte Chemie International Edition*, vol. 54(1), 2015149-154 (https://doi.org/10.1002/anie.201409334). In an 8-dram vial zirconyl chloride hydrate (200 mg) and 4,4',4"-s-Triazine-2,4,6-triyl-tribenzoic acid ($H_3TATB$) (60 mg) were dissolved in DMF (12 mL). Trifluoroacetic acid (0.6 mL) was added to the reaction mixture, and the vial was heated at 120° C. for 4 h. The resulting white solid was then separated by centrifugation (5000 rpm, 5 mins), and washed repeatedly with DMF and acetone. The MOF was dried at 150° C. under vacuum.

Example 3: Synthesis of MIL-101(Fe)

MIL-101(Fe) and MIL-101-$NH_2$(Fe) was synthesized by a modified procedure of the procedure reported in J. Am. Chem. Soc. 2009, 131, 40, 14261-14263. In a 1-L Pyrex jar terephthalic acid (6.58 g) or 2-amino-terephthalic acid (7.17 g) and iron (III) chloride hexahydrate (10.7 g) were dissolved in DMF (900 mL), and to the mixture was added acetic acid (36 mL). The reaction mixture was heated at 110° C. in an oven for 24 h. The resulting solid was separated by centrifugation (5000 rpm, 30 mins), and washed repeatedly with DMF and methanol. The MOF was dried at 150° C. (25° C. for MIL-101-$NH_2$) under vacuum. POST-FUNCTIONALIZATION Example 4: MOF-808-thioglycolic acid (TGA)

To a 100 mL Pyrex jar, MOF-808 (2 g) was added to a solution containing thioglycolic acid (565 mg) and acetone (72 mL). The reaction was left standing at room temperature for 16 h, and the solid was separated by filtration. The solid was then soxhlet extracted with acetone for 16 h. The MOF was dried at 25° C. under dynamic vacuum.

Example 5: MOF-808-T S

In an 8-dram vial MOF-808 (0.25 g) was added to 0.05 M $Na_2S_2O_3$ aqueous solution (25 mL). The reaction was stirred at room temperature for 5 h, and the solid was separated by centrifugation (5000 rpm, 5 mins). The solid was then washed repeatedly with water and then acetone. The MOF was dried at 25° C. under vacuum.

Example 6: PCN-777-TGA

In an 8-dram vial, PCN-777 (0.5 g) was added to a solution containing thioglycolic acid (540 mg) and acetone (15 mL). The reaction was left standing at room temperature for 16 hours, and the solid was separated by centrifugation. The solid was then soxhlet with acetone for 16 h. The MOF was activated at 25° C. under dynamic vacuum.

Example 7: MIL-101-SHPy

MIL-101(Fe) (411 mg) and 4-mercaptopyridine (188 mg) were dissolved in THF (15 mL) in an 8-dram vial. The reaction was stirred at room temperature for 3 h, and the solid was separated by centrifugation. The MOF was washed repeatedly with THE and dried at 25° C. under vacuum.

Example 8: MIL-101-TU

MIL-101-$NH_2$(Fe) (550 mg) was added to a solution containing methyl isothiocyanate (2 mL) and chloroform (15 mL) in an 8-dram vial. The reaction mixture was stirred and heated at 75° C. on a stir plate for 20 h. The solid was then separated by centrifugation (5000 rpm, 15 mins) and washed repeatedly with chloroform. The MOF was dried at 25° C. under vacuum.

Example 9: MOF-808-MPA a. Synthesis of Methylthioacetic Phosphonate

A solution of methyl tosylate phosphonate (1) (25 g, 7 mmol) in DMF (50 ml) was prepared in a 100 ml round bottom flask. Potassium thioacetate (10.6 g, 8.4 mmol) was added in four portions. The solution was heated to 45° C. for 1 hour. Once the reaction was complete, the reaction mixture was extracted 4 times with ethyl acetate (4×80 ml) from 400 ml (1:1 sat NaCl:water) solution. The combined organic layers were dried with $MgSO_4$ and concentrated. Residual DMF was removed by drying under a stream of air overnight. No further purification was necessary. Product was a pale brown oil (16.3 g, 93% yield). $^1$H NMR (500 MHz, $CDCl_3$) δ 4.17-4.08 (m, 4H, $CH_2$), δ 3.22 (d, 2H, $CH_2$, J=14.0 Hz), δ 2.38 (s, 2H, $CH_3$), δ 1.32 (t, 6H, $CH_3$, J=7.0 Hz).

b. Synthesis of MPA

In a glass vial the product of Example 9a (3.53 g, 15.6 mmol) was mixed with 36% HCl (14 ml) and acetic acid (3.7 ml). The solution was capped and put in a 90° C. oven overnight. The solvents were removed by a stream of air for two days. The product was used without further purification (2.18 g, the extra mass is likely because the product was not totally dry). MPA was isolated as an oil, but turned into a white solid after sitting for a few days.

$^1$H NMR (500 MHz, $D_2O$) δ 2.69 (d, 2H, $CH_2$, J=13.0 Hz)

c. Synthesis of MOF-808-MPA

In a 1-L Pyrex jar MPA (0.942 g, 7.35 mmol) was dissolved in DMF (272 mL). MOF808 (5 g dry basis, solvated with DMF) was added and the solution was sonicated and stirred until clumps of MOF were broken up. The jar was then placed in a 50° C. oven overnight and stirred a couple times. The MOF was then filtered and washed with DMF (2× including overnight soak), Acetone (2× including overnight soak), and CHCl3 (2× including 2 hour soak). The MOF was then activated overnight at 100° C. under vacuum. $^1$H NMR analysis showed 2.09 MPA per Zr node. $N_2$ isotherm had an uptake of 431 $cm^3/g$.

Example 10: Pd Scavenging Test

Into an 8-dram vial there was added 25 mg of solid adsorbent (MOF or reference material) and a stir bar. To this there was added 8 mL of the solution to be purified on top of the adsorbent. The solution contained varying amounts of Pd as $Pd(OAc)_2$ dissolved in THF, either alone (Table 1) or with ibuprofen at 20 mg/mL added (Table 2). The vial was stirred for 30 mins and then the solution was filtered through a syringe filter (220 nm, PTFE). The filtrate was then analyzed to determine the Pd concentration either by Inductively Coupled Plasma (ICP) or UV-Vis. Spectrometry. The results of the experiments are presented in Table 1 and Table 2.

TABLE 1

Scavenging Ability of Various Adsorbent for Pd

| Scavenger | Final Pd concentration (ppm) | Final Pd Concentration (300 ppm)[3] | Capacity from 300 ppm test (mg Pd/g adsorb.) |
|---|---|---|---|
| Initial Pd Concentration | 100 ppm | 300 ppm | |
| MP-TMT[1] | 54.3[4] | 274[3] | 8.32 |
| Si-TMT[1] | 53.3[4] | 215[3] | 27.2 |
| MOF-808 TGA | LOD[2,4] | 132[3] | 69.4 |
| MOF-808 TS | 8[3] | 180[3] | 38.4 |
| PCN-777 TGA | 15.7[3] | Not Tested | Not Tested |
| MIL-101SHPy | 14.13[3] | Not Tested | Not Tested |
| MIL-101-TU | 0.39[3] | 31[3] | 86.1 |
| MOF-808-MPA | LOD[4] | 76[4] | |

[1]Obtained from Biotage: MP-TMT is a polystyrene bound 2,4,6-trimercaptotriazene; Si-TMT is a silica bound 2,4,6-trimercaptotriazene.
[2]LOD: below detection limit (0.1 ppm).
[3]UV-Vis Result
[4]ICP-Result The results in Table 1 show the advantages of the MOFs of the invention. They are observed to remove more Pd than commercially available adsorbents.

TABLE 2

Scavenging Ability of Adsorbents from a Solution containing Pd and Ibuprofen[1]

| Scavenger | Pd Conc. (ppm)[2] |
|---|---|
| MP-TMT | 81 |
| Si-TMT | 75 |
| MIL-101-TU | 5 |

[1]The test solution contained 100 ppm Pd as Pd(OAc)$_2$ and 20 mg/mL of ibuprofen
[2]Analysis was done by UV-Vis spectrometry.

The results presented in Table 2 show that MIL-101-TU is a much better scavenger than commercially available adsorbents in the presence of a pharmaceutically active ingredient.

We claim as our invention:

1. A process comprising:
   contacting a feed stream comprising an active pharmaceutical ingredient (API) and a contaminant with an adsorbent at purification conditions to adsorb at least a portion of at least one contaminant onto the adsorbent and provide a. purified API stream; wherein said at least one contaminant is an elemental impurity selected from at least one element from class 1, class 2A, class 2B, and class 3 of the ICH Q3D(R1) guidelines;
   wherein the adsorbent is a metal-organic framework (MOF) comprising metal ion corner atoms and a linker molecule which is at least a bidentate ligand, the MOF further having at least one functional moiety which is able to bind with said at least one contaminant in the feed solution;
   where the metal ion is selected from $Ti^{4+}$, $Zr^{4+}$, $Fe^{3+}$, $Co^{3+}$, $Ni^{2+}$, $Cu^{2+}$, $Zn^{2+}$, $Al^3$ and mixtures thereof;
   wherein the linker molecule comprises at least one ligand selected from 1,3,5-benzene tricarboxylic acid (BTC), acetylenedicarboxylate (ADC), naphtalene dicarboxylate (NDC), benzene dicarboxylate (BDC), adamantane tetracarboxylate (ATC), benzene tribenzoate (BTB), methane tetrabenzoate (MTB), adamantane tribenzoate (ATB, terephthalic acid, 2-amino terephthalic acid, 4,4',4'',4'''-(pyrene-1,3,6,8-tetrayhtetrabenzoic acid (TBAPy), meso-Tetraphenylporphine-4,4',4'',4'''-tetracarboxylic acid (TCPPH2), 4,4',4''-s-Triazine-2,4,6-triyl-tribenzoic acid (H3TATB), and 1,4-diazabicyclo[2.2.2]octane (DABCO), and mixtures thereof;
   wherein the functional moiety is selected from thiogiycolic acid (TGA), thiourea, 4-mercapto pyridine, 2,4,6,-trimercaptotriazine (TMT), 1,4,7,10-Tetraazacyclododecane- 1,4,7,10-tetraacetic acid (DOTA), ethylenediaminetetraacetic acid (EDTA), thiosulfate (TS), mercapto phosphonic acid, and mixtures thereof; and
   wherein the feed stream comprises an organic solvent.

2. The process of claim 1 where the adsorbent adsorbs a quantity of the elemental impurity in the feed stream to provide a purified API stream having a concentration of the elemental impurity which calculates to a concentration of the elemental impurity in a recovered API which is at or below its Permitted Daily Exposure (PDE).

3. The process of claim 1 where the adsorbent is formed into a shape selected from pellets, spheres, disks, irregularly shaped particles, extrudates, and mixtures thereof.

4. The process of claim 1 where the adsorbent is admixed with the feed stream in a vessel and contacted at purification conditions to provide a purified stream.

5. The process of claim 4 where the adsorbent is present in an amount from about 0.1 weight of adsorbent/weight of stream % (w/w %) to about 70 w/w %.

6. The process of claim 4 where the purification conditions comprise a temperature from about −50° C. to about 120° C., a pressure of about 0.01kPa to about 1000kPa and a contact time from about 5 seconds to about 3 days.

7. The process of claim 1 where the adsorbent is in a bed and the feed stream is flowed through it.

8. The process of claim 7 wherein the bed is in the form of at least one column and the feed stream is flowed through the at least one column at a linear velocity from about 0.02 cm/min. to about 300 cm/min.

9. The process of claim 1 where the feed stream is contacted with the adsorbent at a pressure from about 0.01kPa to about 1000 kPa.

10. The process of claim 7 where the feed stream is flowed through the adsorbent bed in a single pass.

11. The process of claim 1 where the adsorbent is contacted with the teed stream at a temperature from about −50°C, to about 120° C.

12. The process of claim 1 where the adsorbent is a mixture of at least two MOFs.

13. The process of claim 1 where the functional moiety is bonded to a metal site.

14. The process of claim 1 where the functional moiety is covalently bonded to the framework.

15. The process of claim 1 where the MOF with functional moiety is selected from MOF-808-TGA, MOF808-TS, MOF-808-TU, MOF-808-SHPy, MOF-808-MPA, PCN-777-TGA, PCN-777-TS, PCN-777-TU, MIL-101-SHPy, MIL-101-TGA, MIL-101-TS, MIL-101-TU, and mixtures thereof.

16. The process of claim 1 wherein the elemental impurity comprises palladium and the functionalized MOF has a capacity for palladium of at least 35.0 mg Pd/g.

17. The process of claim 1 wherein said MOF with functional moiety is selected from MOF808-TS, MOF-808-TU, MOF-808-SHPy, MOF-808-MPA, PCN-777-TGA, PCN-777-TS, PCN-777-TU, MIL-101-SHPy, MIL-101-TGA, MIL-101-TS, MIL-101-TU, and mixtures thereof.

* * * * *